(12) United States Patent
Loraine

(10) Patent No.: US 11,230,689 B2
(45) Date of Patent: Jan. 25, 2022

(54) SYSTEM AND METHOD FOR GENERATING AND STORING METHANE GAS USING RENEWABLE SOURCES

(71) Applicant: Native American Construction Service, Inc., Eagle Mountain, UT (US)

(72) Inventor: Christian René Loraine, Eagle Mountain, UT (US)

(73) Assignee: Native American Construction Service, Inc., Eagle Mountain, UT (US)

( * ) Notice: Subject to any disclaimer, the term of this patent is extended or adjusted under 35 U.S.C. 154(b) by 662 days.

(21) Appl. No.: 15/986,757

(22) Filed: May 22, 2018

(65) Prior Publication Data

US 2018/0355301 A1     Dec. 13, 2018

Related U.S. Application Data

(60) Provisional application No. 62/516,410, filed on Jun. 7, 2017.

(51) Int. Cl.
  *C12M 1/107*   (2006.01)
  *F17C 9/00*    (2006.01)
  (Continued)

(52) U.S. Cl.
  CPC .............. *C12M 23/36* (2013.01); *B01F 9/06* (2013.01); *B01F 15/027* (2013.01); *C12M 21/04* (2013.01);
  (Continued)

(58) Field of Classification Search
  None
  See application file for complete search history.

(56) References Cited

U.S. PATENT DOCUMENTS

| | | | |
|---|---|---|---|
| 2,198,737 A | 4/1940 | Petersen | |
| 4,100,023 A * | 7/1978 | McDonald | C02F 3/301 435/167 |

(Continued)

FOREIGN PATENT DOCUMENTS

| | | |
|---|---|---|
| DE | 3325257 | 1/1985 |
| WO | WO 2012/116394 | 9/2012 |
| WO | WO 2012/172329 | 12/2012 |

OTHER PUBLICATIONS

International Search Report and Written Opinion, dated Aug. 8, 2018, 10 pages, from the International Searching Authority, for the corresponding International Application No. PCT/US2018/034220.

*Primary Examiner* — William H. Beisner
(74) *Attorney, Agent, or Firm* — Polsinelli LLP

(57) ABSTRACT

Systems and methods provide a self-contained sealed apparatus that captures, filters, compresses and stores methane gas produced by the decomposition of bio-degradable organic materials. The system includes a rotatable and sealable chamber with an intermittent drive unit that mixes moist bio-degradable material during an anaerobic reaction, and captures methane gas generated by anaerobic decomposition. A filter to remove impurities, a low-pressure storage tank, a compressor and a high-pressure storage tank are interconnected and controlled by a system that monitors system parameters, that may include gas flow rate, temperature, and gas volume, and controls system parameters, that may include drive unit activation, generator operation, and compressor operation.

14 Claims, 9 Drawing Sheets

(51) Int. Cl.
  *F17C 5/06* (2006.01)
  *B01F 9/06* (2006.01)
  *C12M 1/00* (2006.01)
  *C12M 3/04* (2006.01)
  *F17C 3/02* (2006.01)
  *B01F 15/02* (2006.01)
  *B01D 53/04* (2006.01)
  *B01D 53/14* (2006.01)
  *B01F 9/00* (2006.01)

(52) U.S. Cl.
  CPC ............ *C12M 27/10* (2013.01); *C12M 27/20* (2013.01); *C12M 29/04* (2013.01); *C12M 29/14* (2013.01); *C12M 47/18* (2013.01); *F17C 3/022* (2013.01); *F17C 5/06* (2013.01); *F17C 9/00* (2013.01); *B01D 53/04* (2013.01); *B01D 53/1418* (2013.01); *B01D 2252/103* (2013.01); *B01D 2253/102* (2013.01); *B01F 2009/0063* (2013.01); *B01F 2215/0073* (2013.01); *F17C 2205/0341* (2013.01); *F17C 2221/033* (2013.01); *F17C 2223/0123* (2013.01); *F17C 2223/033* (2013.01); *F17C 2225/0123* (2013.01); *F17C 2225/035* (2013.01); *F17C 2227/0157* (2013.01); *F17C 2250/043* (2013.01); *F17C 2250/046* (2013.01); *F17C 2250/0439* (2013.01); *F17C 2250/0443* (2013.01); *F17C 2260/04* (2013.01)

(56) References Cited

U.S. PATENT DOCUMENTS

| | | | |
|---|---|---|---|
| 4,223,094 A * | 9/1980 | Vaseen ................ | C12M 21/02 435/298.2 |
| 4,836,737 A | 6/1989 | Szikriszt | |
| 5,244,274 A * | 9/1993 | Onodera ................ | B65F 3/00 366/147 |
| 5,890,664 A * | 4/1999 | Conant, III ........... | C05F 17/929 241/33 |
| 6,178,899 B1 | 1/2001 | Kaneko et al. | |
| 2005/0061001 A1* | 3/2005 | Maston ................ | C12M 47/18 60/649 |
| 2007/0190643 A1* | 8/2007 | Noll ....................... | C12M 23/50 435/290.3 |
| 2015/0031104 A1* | 1/2015 | Eggersmann .......... | C12M 21/04 435/167 |

* cited by examiner

SYSTEM AND METHOD FOR GENERATING AND STORING METHANE GAS USING RENEWABLE SOURCES

CROSS-REFERENCE TO RELATED APPLICATIONS

This application claims priority to U.S. Provisional Patent Application Ser. No. 62/516,410, filed Jun. 7, 2017, entitled System and Method for Generating and Storing Methane Gas Using Renewable Sources, the entire content of which is incorporated herein by reference.

BACKGROUND

There are a number of renewable energy sources, and technologies to take advantage of those sources. Some of the technologies require significant capital investment (such as wind), and some technologies have limits on where they can be used. Systems and methods are needed that have a smaller footprint, are generally self-contained, and can exploit locally available renewable natural resources, all without significant capital investment.

The preceding description is not to be construed as an admission that any of the description is prior art relative to the present invention.

SUMMARY OF THE INVENTION

In one aspect, a system and method include an apparatus with a sealable chamber. The sealable chamber includes at least a plurality of internal mixing blades and a gas connection that is configured to allow passage of gas from the chamber. The apparatus further includes a drive unit that is configured to at least intermittently rotate the chamber, and a filter that is configured to filter the gas. The apparatus further includes a first gas storage tank that is configured to store the gas.

In a further aspect, the system and method include a second gas storage tank and a compressor that is connected to both the first gas storage tank and the second gas storage tank. The compressor is configured to compress and transfer the gas from the first gas storage tank to the second gas storage tank. In a further aspect, the system and method include a sensor that is configured to activate the compressor based at least on volume of gas in the first gas storage tank. In a further aspect, the system and method include a generator configured to burn the gas. In a further aspect, the system and method include a generator configured to provide power to the drive unit. In a further aspect, the system and method include a removable cover for the sealable chamber. In a further aspect, the system and method include a gas connection. In a further aspect, the chamber is cylindrical. In a further aspect, the internal mixing blades are attached to an inner surface of the chamber, and are configured to mix material in the chamber when the chamber is rotated. In a further aspect, the filter is an activated charcoal filter or a water bubble filter. In a further aspect, the system and method include a control unit configured to cause activation of a compressor. In a further aspect, the system and method include a control unit configured to cause activation of a generator. In a further aspect, the system and method include a control unit that receives data representing at least one of a temperature value inside the chamber, a temperature value outside the chamber, a gas flow rate, a moisture level of material inside the chamber or a gas volume inside the first gas storage tank. In a further aspect, the system and method further include at least one battery configured to provide power to the drive unit. In a further aspect, the system and method further include a support mount for the chamber that is configured to hold a rotational axis of the chamber at an inclined axis to a local earth surface.

The foregoing specific aspects are illustrative of those which can be achieved and are not intended to be exhaustive or limiting of the possible advantages that can be realized. Thus, the objects and advantages will be apparent from the description herein or can be learned from practicing the invention, both as embodied herein or as modified in view of any variations which may be apparent to those skilled in the art. Accordingly the present invention resides in the novel parts, constructions, arrangements, combinations and improvements herein shown and described.

BRIEF DESCRIPTION OF THE DRAWINGS

The foregoing features and other aspects of the invention are explained in the following description taken in conjunction with the accompanying figures wherein.

It is understood that the drawings are for illustration only and are not limiting.

DETAILED DESCRIPTION OF THE DRAWINGS

The various embodiments described herein, provide systems and methods for processing bio-degradable organic material to produce combustible fuel, such as methane. The systems described are generally self-contained, in that power to operate the system is produced by a generator burning some of the combustible fuel that is produced by the system. Although the system can be scaled in size, in at least one embodiment, the system can be moved and is portable, such as on a trailer.

Figure 1:
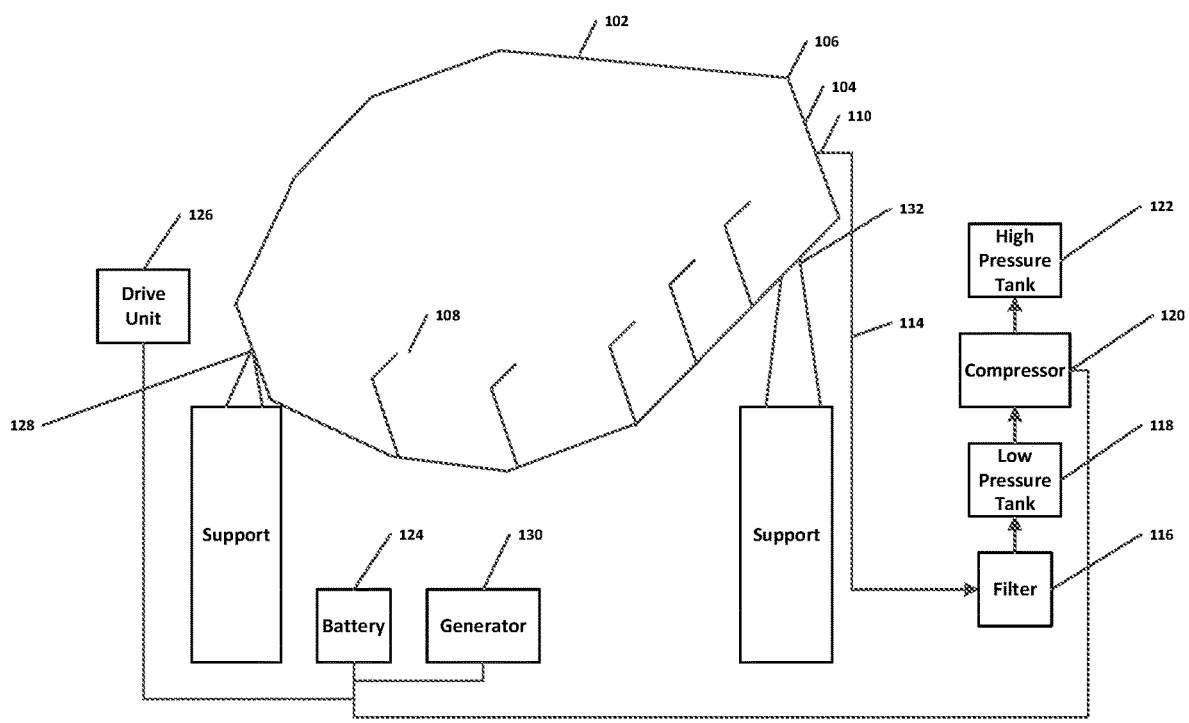
FIG. 1 illustrates embodiments of a system.

In one embodiment, system 100 is comprised of various components, examples of which are illustrated generally in FIG. 1. As illustrated, system 100 includes a chamber 102. In at least one embodiment as illustrated, chamber 102 is generally cylindrical, and tapered on each end. At one end, chamber 102 includes a sealable cover 104. To assist with sealing cover 104 to chamber 102, a gasket 106 is provided.

In operation, bio-degradable materials, such as vegetable/plant matter, or animal waste are placed inside chamber 102, and the chamber is sealed with gasket 106 and cover 104. As the bio-degradable material decomposes, it produces by-products, such as methane, which can be used as a fuel source. To assist with production of the methane, chamber 102 includes internal mixing blades 108. When chamber 102 is rotated, the mixing blades 108 turn and mix the bio-degradable material.

Figure 2:
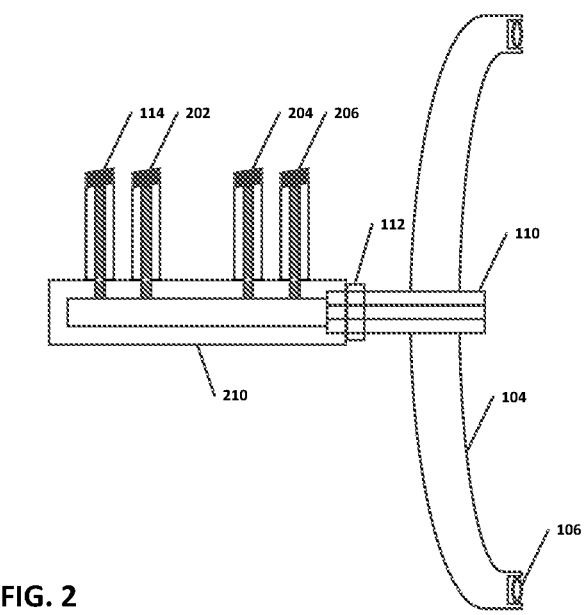
FIG. 2 illustrates embodiments of a system.

As illustrated in FIGS. 1 & 2, to assist with removal of methane from the chamber and for other purposes, a connection 110, is provided in cover 104. Connection 110 includes a passage for gas or fluid and includes a rotatable seal 112. Connection 110 is rotatable within manifold 210.

Manifold 210 includes piping 114 that routes methane gas to a filter 116, a low-pressure storage tank 118, a compressor 120, and a high-pressure storage tank 122. Manifold 210 also includes a vent connection 202, a H2O connection 204, and a CO2 connection 206. Although not illustrated, connections 114, 202, 204 and 206 are each routed to individual control valves, and in some implementations, those control valves can be opened and closed using electronic signals.

Chamber 102 is angled with respect to the horizon. This configuration helps keep cover 104 above most of the mass of the bio-degradable material. This configuration also keeps gas connection 110 above most of the mass of the bio-degradable material. In one embodiment the angle of chamber 102 with respect to the horizon is about 8 degrees, although other angles may be appropriate.

Power for operation of system 100 is generally provided by battery 124, which may be one or more deep cycle batteries. Battery 124 provides electrical power to operate drive unit 126, where drive unit 126 may include a geared electric motor. Drive unit 126 is mechanically connected to one end of chamber 102. There are a number of ways for the mechanical connection of drive unit 126 to chamber 102, including direct, belt, gear, or chain drive.

The direction of rotation provided by drive unit 126 is reversible. The speed of rotation provided by drive unit 126 is also variable in both directions. In one direction of rotation, the bio-degradable material is primarily mixed or turned by mixing blades 108. In the opposite direction of rotation, mixing blades 108 primarily move the bio-degradable material toward an opening on one end of chamber 102, and if rotation continues, the bio-degradable material is moved up and out of chamber 102 through the opening. Cover 104 covers that same opening. In one direction, where mixing blades 108 primarily mix or turn the bio-degradable material, the speed of rotation is generally low to minimize power requirements. In the other direction, where mixing blades 108 primarily move the bio-degradable material toward the opening on one end of chamber 102, the speed of rotation is higher than the other direction.

Rotational support for one end of chamber 102 is provided by bearing 128. Support for the other end of chamber 102 is provided by a trunnion with pair of track bearings 132. In other implementations, support for one end of chamber 102 may be integrated with manifold 210.

In operation, the system is semi-autonomous, providing a sealed system that directs a gas byproduct from the anaerobic digestive process. A substantial portion of the gas is CH4, which passes through filter to 116 reduce impurities, including sulfur. After passing through filter 116, the gas enters low-pressure storage tank 118. Sensors associated with low-pressure storage tank 118 determine when the level of stored gas has reached a specified capacity, and then the gas is pressurized and transferred to high-pressure storage tank 122. Pressurization and transfer of the gas from low-pressure storage tank 118 to high-pressure storage tank 122 is provided by compressor 120. Regular intermittent mixing of the bio-degradable material yields a greater gas production, as well as more efficient consumption of the bio-degradable material. With the exception of loading the bio-degradable material into chamber 102, and unloading the bio-degradable material from chamber 102, the system is generally sealed, and self-regulated.

Chamber 102 is mounted on an inclined angle or plane to aid in the rotation of the drum, while simultaneously being able to discharge, siphon or withdraw the gas. In some aspects, the inclined angle is close to horizontal, and might be less than 10 degrees. An inclined angle of approximately 8 degrees has shown some advantages, particularly for loading and unloading. Other angles may provide other advantages, and in some other aspects, the inclined angle is closer to vertical, and may even be vertical. Chamber 102, which is generally in the shape of a drum, has internal helically inclined mixing blades 108 that are affixed to the interior wall of the drum. This allows the drum to mix, when rotated in one direction, and discharge, when rotated in the opposite direction. Chamber or drum 102 is covered with a hatch-like cover 104, and sealed with gasket 106, which helps to prevent escape of the gas and prevent entry of oxygen into chamber 102.

Gas that is generated by the decomposition is removed or allowed to flow from chamber 102 through a discharge or siphon hose. One end of the discharge or siphon hose is connected to gas connection 110 on cover 104 through connection 114. Connection 114 in manifold 210 is connected to filter 116 by discharge or siphon hose. Filter 116 is an in-line filter. In one aspect, the filter material is clean water, which absorbs sulfuric byproduct that is bonded with the gas and absorbs impurities. In another aspect, the filter material is activated carbon, which also absorbs impurities. Filter 116 also filters deleterious particulate components by trapping them in the water or the activated carbon. Once the gas has passed through filter 116, the gas is transferred by hose to low-pressure storage tank 118.

Although not illustrated, or required, in some embodiments the gas is dried before it is transferred to the low-pressure storage tank. The gas dryer might use a hygroscopic material, or some other technique.

The low-pressure storage tank 118 is a bladder tank, with directional valves that keep gas from back flowing into chamber 102. The low-pressure storage tank expands and contracts with varying amounts of gas, and sensors associated with the low-pressure storage tank provide signals that serve to actuate compressor 120. Compressor 120 both compresses, and transfers the gas to high-pressure storage tank 122, and when low-pressure storage tank 118 is empty or less than full, compressor 120 turns off.

The connection of the discharge or siphon hose to cover 104 is with gas connection 110. The gas connection allows the chamber and cover to rotate while the discharge or siphon hose remains stationary. FIG. 2 illustrates one embodiment of gas connection 110, manifold 210, cover 104, seal 122, and connections 202, 204, and 206.

Once the gas has been filtered and compressed, it can be used for heating and cooking, or for providing power. Compressed gas from the high-pressure storage tank can also provide an energy source for generator 130. In one embodiment, generator 130 burns some of the gas to produce electricity for general use and to charge battery 124. In another embodiment, generator 130 is smaller and burns gas and operates to charge battery 124. Battery 124 is one or more deep cycle batteries, and provides power for the electrical components, including drive unit 126, compressor 120, as well as a computer 302 and other control system electronics.

Drive unit 126 is a DC motor that is geared to provide about 8 rpm output rotation of chamber 102 when operating in the forward direction. In the reverse direction, drive unit 126 provides approximately 8 rpm of rotation for chamber 102.

Figure 3:
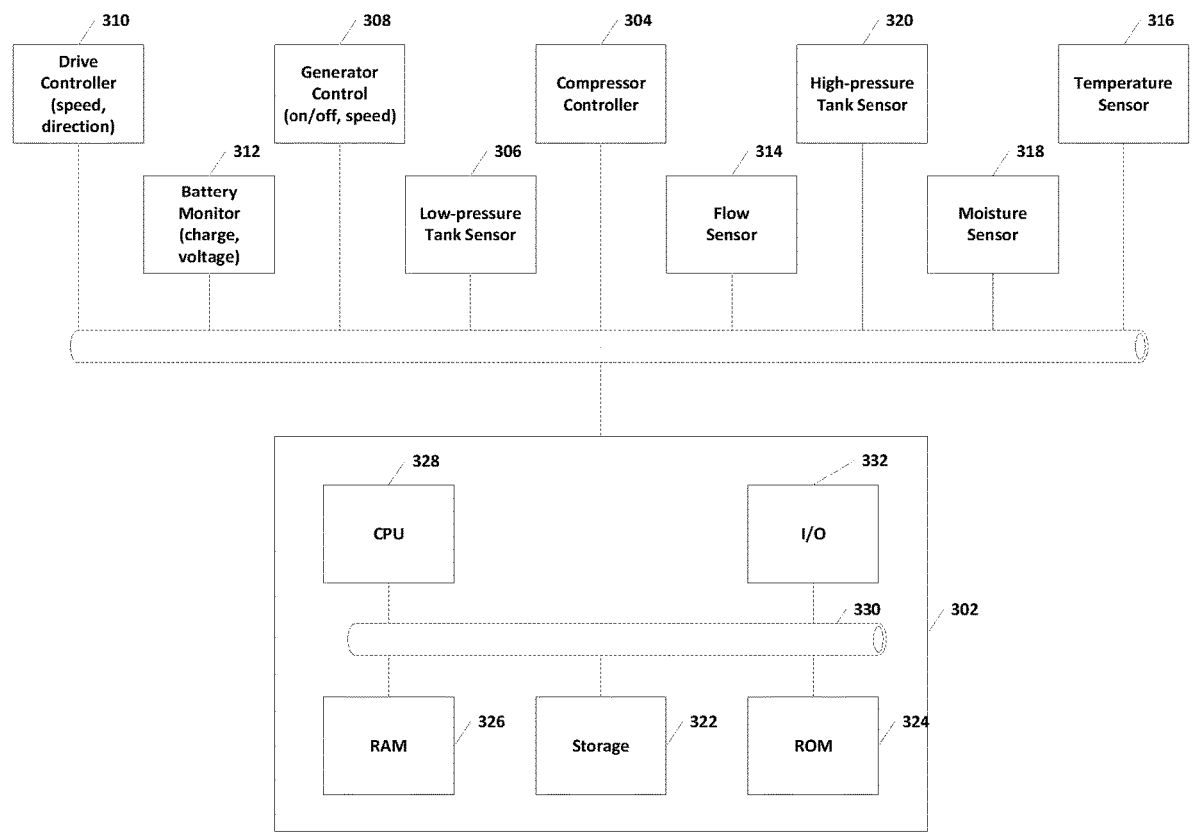
FIG. 3 illustrates embodiments of a system.

Referring to FIGS. 1 & 3, control of the system is provided by a programmed computer 302 that monitors various pressures, temperatures, flow rates, and moisture levels, and adjusts system parameters based on the measured values. In particular, low-pressure tank sensor 306 associated with the low-pressure storage tank provides a signal to computer 302. Computer 302 determines from that signal that the low-pressure storage tank is full or getting full, and sends a signal to compressor control 304 to activate compressor 120. When signals from low-pressure tank sensor 306 indicates that gas in low-pressure storage tank 118 has been removed, or reaches a specified quantity or level, computer 302 then sends signal(s) to turn compressor 120 off using compressor control 304.

Battery monitor 312 provides signals that reflect the charge state of battery 124, and computer 302 uses those signals to determine when to charge the battery. When charging is needed, computer 302 sends signals to generator control 308, which serve to activate generator 130. Generator 130 burns some of the stored gas to generate DC power, which is used to charge battery 124, as necessary. Computer 302 also intermittently activates drive unit 126, by sending signals to drive controller 310. Those signals cause drive unit 126 to mix/turn the bio-degradable material.

Computer 302 also monitors the flow of gas from chamber 102, using flow sensor 314. In addition, computer 302 monitors temperature and moisture levels of the bio-degradable material, using temperature sensor 316 and moisture sensor 318. Computer 302 also receives signals from high-pressure tank sensor 320, which reflects pressure of gas stored in high-pressure storage tank 122.

Computer 302 may be a general purpose computer, such as a PC, or it may be a micro-processor. Computer 302 includes data/code storage data/code 322, which is used to store computer executable software, and data. In some embodiments, computer 302 also includes Read-Only-Memory (ROM) 324, and Random-Access-Memory (RAM) 326, which are connected to one or more central processing unit(s) (CPU) 328 by a computer bus 330. Computer 302 may also include one or more input/output devices 332, such as a keyboard, a mouse, a display, or a printer.

In the embodiments illustrated in FIG. 3, computer 302 is a single computer that provides a unified system control and is connected to all system sensors and controllers. However, in other embodiments, computer 302 may be multiple computers some of which are interfaced with each other, and others are not interfaced to any other part of the system. For example, drive controller 310 may be a self-contained computer or timer that monitors time, and activates drive unit 126 based on time elapsed since the drive unit was previously active. Similarly, battery monitor 312 may measure the voltage of battery 124, and activate a battery charge circuit when the battery voltage falls to a specified level. Likewise, compressor controller 304 may only receive signals from the low-pressure tank sensor 306, and activate compressor 120 without regard to any other part of the system.

Figure 4:
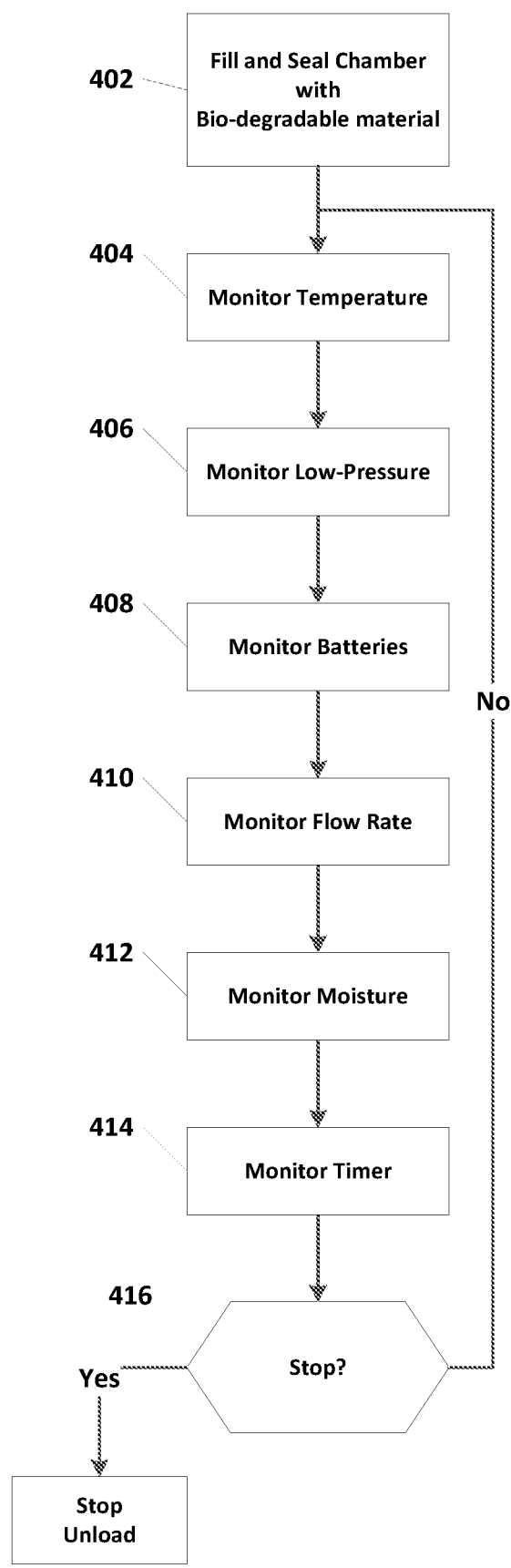
FIG. 4 illustrates embodiments of steps in a method.
Figure 5:
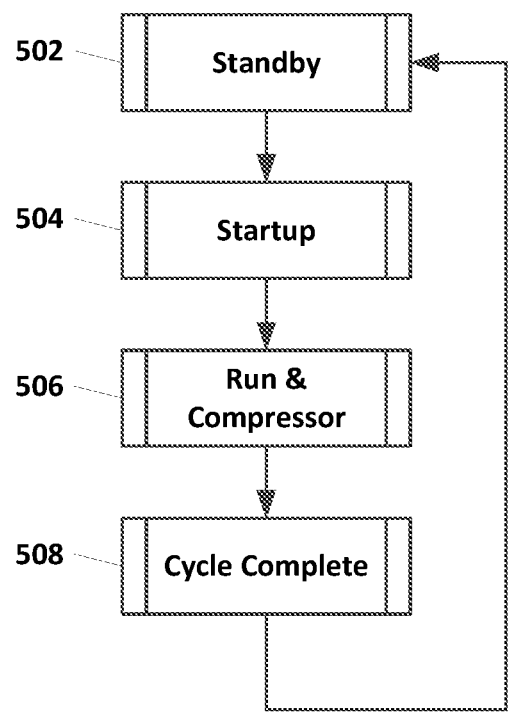
FIG. 5 illustrates embodiments of steps in a method.

FIG. 4 illustrates steps in a method according to one embodiment. At step 402, chamber 102 is filled with bio-degradable materials, and an appropriate quantity of water may be added, cover 104 with gasket 106 are placed on chamber 102, and sealed.

At 404, computer 302 monitors temperature of the bio-degradable materials using signals from temperature sensor 316. The process that generates the methane gas generally occurs in the absence of oxygen, and it also generates heat. In some embodiments, keeping the temperature of the bio-degradable materials between about 110 and 130 degrees F. seems to generate satisfactory output. Depending on how well insulated the system is, and the ambient temperature, it may be appropriate to adjust parameters that either increase or decrease the temperature inside the chamber to maintain the temperature within a desired range. For example, if the temperature needs to be decreased, activating fans that blow on or around the chamber might help to reduce the temperature. Alternatively, if the temperature needs to be increased, burning some of the methane to produce heat that is then transferred to the chamber might help to increase the temperature.

At 406, computer 302 monitors the low-pressure storage tank using signals from low-pressure tank sensor 306. The low-pressure tank sensor generally detects the level of a fluid that is displaced as methane gas fills a flexible bladder. In this way, the sensor provides an indication of the quantity of gas that is in the low-pressure storage tank. When the sensor provides a signal that indicates the low-pressure storage tank is full or close to full, the system activates compressor 120 by using compressor controller 304. Compressor 120 pulls or extracts methane from low-pressure storage tank 118, compresses the methane, and transfers the compressed methane gas to high-pressure storage tank 122. This continues until low-pressure tank sensor 306 indicates that the low-pressure storage tank is empty or nearly empty, at which point the system turns compressor 120 off by using compressor controller 304.

At 408, computer 302 monitors the battery charge state using signals from battery monitor 312. Battery monitor 312 generally measures voltage of battery 124, although it may also monitor current from battery 124 under a known load. For a deep cycle battery bank, the measured voltage both with and without a known load, can provide an estimate of the state of charge. It is also possible to determine the state of charge using voltage alone. When the system determines that the battery charge has declined to a specified threshold, the system activates or starts generator 130 by using generator controller 308. Once the battery charge level reaches a second specified threshold, the system stops the battery charging by stopping generator 130 with signals from generator controller 308. In one embodiment, generator 130 runs on methane and is the same generator that provides electricity for general use. Alternatively, generator 130 may only be used to charge the batteries. Similarly, it may be appropriate to use a solar cell and controller to maintain the charge on battery 124. In one embodiment, the battery pack is sized so that it only needs to be recharged every few weeks or months. Or, the battery pack may be sized along with a solar charger so they keep the battery pack at an optimal level.

At 410, computer 302 monitors the flow rate of gas from chamber 102 using signals from flow sensor 314. In some embodiments, the system does not try to adjust parameters that would affect the production of methane, and the flow rate monitor is simply to determine how much methane is being produced and the rate of production, and possibly provide alarms if the rate becomes too high, or too low. Alternatively, the system may adjust parameters based on the flow rate. For example, because temperature can change the rate of methane production, the system may monitor temperature and flow rate, and adjust the temperature based on flow rate to thereby modulate the process. Or, the system may adjust the rate or duration of mixing based on measured flow rate. For example, if the flow rate is higher than desired, the system may increase the intervals between mixing cycles, which can slow the process. Or, if the flow rate is lower than desired, the system may decrease the intervals between mixing cycles, to speed the process.

At 412, computer 302 monitors the moisture level of the bio-degradable materials using signals from moisture sensor 318. Generally, the system and process provide the best results when the moisture content is between 50 and 60 percent. That moisture level is generally established when the bio-degradable material is initially loaded in chamber and before the chamber is closed and sealed. As a result, the system does not generally adjust parameters based on measured moisture content. However, in some instances moisture may be added after the chamber is closed, and in those circumstances there may be instances where the system determines that adding moisture will be advantageous, and the signals from moisture sensor 318 can be used to determine when that appropriate time occurs. In other embodiments that amount of moisture may be calculated from the chamber size and mass of bio-degradable material loaded in the chamber.

At 414, computer 302 monitors time since the chamber was closed and sealed, using a timer. It is possible to determine the approximate quantity of methane that can be produced by a given quantity of bio-degradable material. If the flow rate is monitored, the amount of methane produced to date can be determined, and if that information is used with the time since closed and sealed it is possible to determine the approximate time that the system will continue to produce methane before it needs to be reloaded.

At 416, computer 302 determines whether the gas production rate from the bio-degradable materials has declined to a specified level, and if so, the process stops, and unloads the bio-degradable materials from chamber 102, after cover 104 is removed.

FIGS. 5-10 illustrate additional implementations and methods. The gas production cycle may include a standby mode 502, a startup mode 504, a run and compressor mode 506, and a cycle complete mode 508. Once the system has completed a cycle at 508, it returns to standby mode 502.

Figure 6:
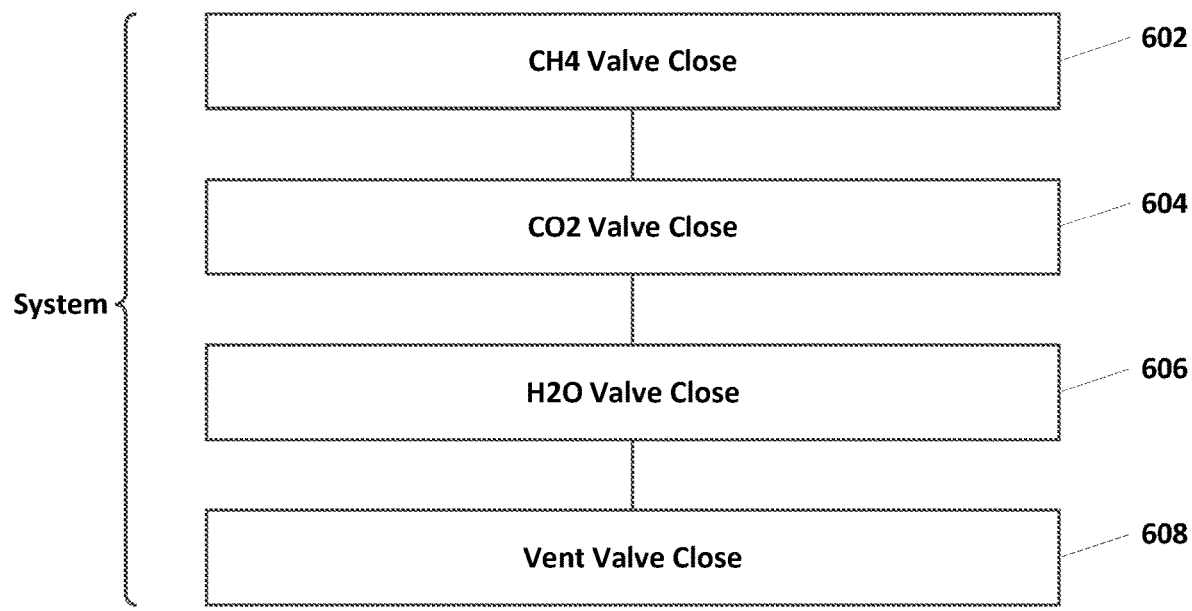
FIG. 6 illustrates embodiments of steps in a method.

Standby mode 502 is illustrated further in FIG. 6, where a methane gas valve that is connected to 114 on manifold 210 is closed at 602. Also in the standby mode, a valve that is connected to vent connection 202 on manifold 210 is closed. At 606 in standby mode a valve that is connected to water connection 204 on manifold 210 is closed, and a valve that is connected to carbon dioxide gas connection 206 is also closed. Steps 602-608 in FIG. 6 are generally performed or controlled by computer 302 of the system.

Figure 7:
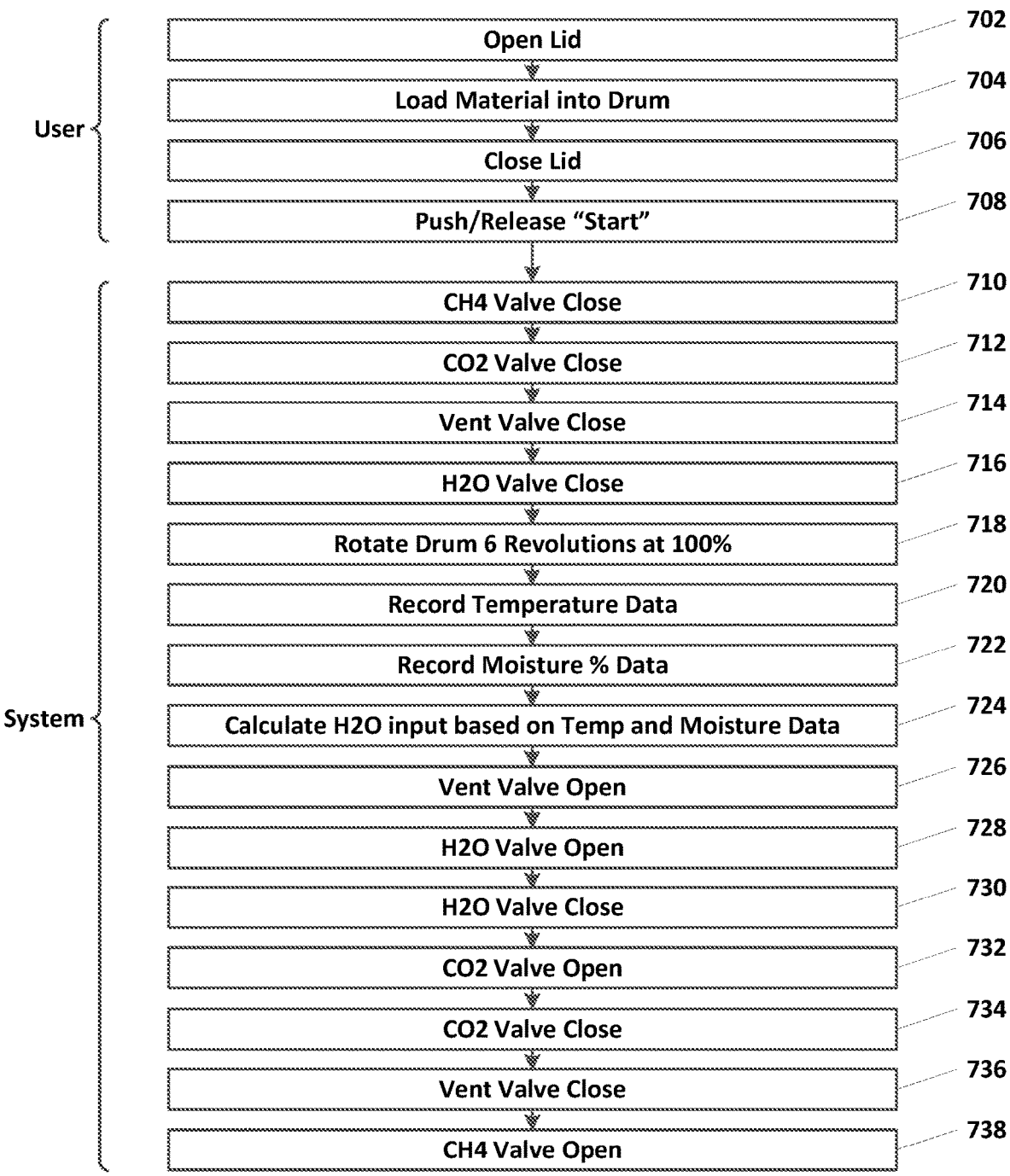
FIG. 7 illustrates embodiments of steps in a method.

Startup mode 504 is illustrated further in FIG. 7. At 702, a user opens lid 104 and at 704 the user loads bio-degradable material into chamber 102. At 706, the user closes and seals lid 104, and at 708 activates the system by pressing and releasing a start button.

After the user presses and releases the start button, computer 302 causes the methane gas valve that is connected to 114 of manifold 210 to close. In a similar matter at 712, 714 and 716, computer 302 causes the vent valve, water valve and carbon dioxide valves that are connected to respective connections 202, 204 and 206 to also close.

At 718, computer 302 causes the drive controller to activate and rotate the chamber for a determined number of turns. In one aspect this is six rotations at 100% rotation speed.

At 720, computer 302 determines and records data corresponding to the temperature, and at 722 determines and records data corresponding to the moisture percentage.

At 724, based on the temperature and moisture percentage, computer 302 calculates a quantity of water that should be added and mixed with the bio-degradable material. At 726, the valve that is connected to vent connection 202 of manifold 210 is opened, and at 728 the valve that is connected to water connection 204 of manifold 210 is also opened. The water valve is held open until the calculated quantity of water has been added to chamber 102, and then at 730 the water valve is closed.

At 732, the valve that is connected to carbon dioxide connection 206 is opened, and the carbon dioxide valve is held open for a period of time that will allow the carbon dioxide to substantially displace air in chamber 102 and replace the air with carbon dioxide. At that time, the carbon dioxide valve is closed at 734. The vent valve is closed at 736 and the methane gas valve is opened at 738.

Steps 702-708 are generally performed by a user, while steps 710-738 are generally performed or controlled by computer 302 of the system.

When the startup mode 504 is completed, the system operates in the run and compressor mode 506. These modes are further illustrated in FIGS. 8 and 9.

At 802 in the run mode, computer 302 causes the chamber to rotate on a periodic basis. In one implementation, the chamber is rotated 1 revolution at 50% speed once every six hours. At 804 and 806 also during the run mode, computer 302 measures and records data representing the temperature and data representing the moisture percentage. Those measurements are taken and recorded every 30 minutes.

Also during the run mode, computer 302 monitors the low pressure tank and when it is full or needs to be emptied at 902, the computer closes the methane valve at 904, and activates the compressor at 906. When computer 302 determines that the low pressure tank is empty at 908, the compressor is deactivated at 910, and at 912, the methane valve is opened.

Figure 8:
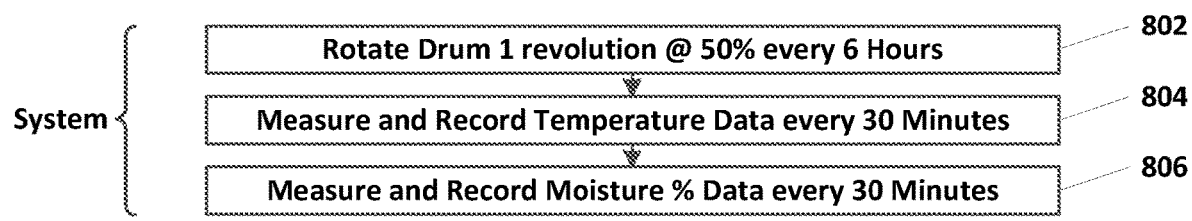
FIG. 8 illustrates embodiments of steps in a method.
Figure 9:
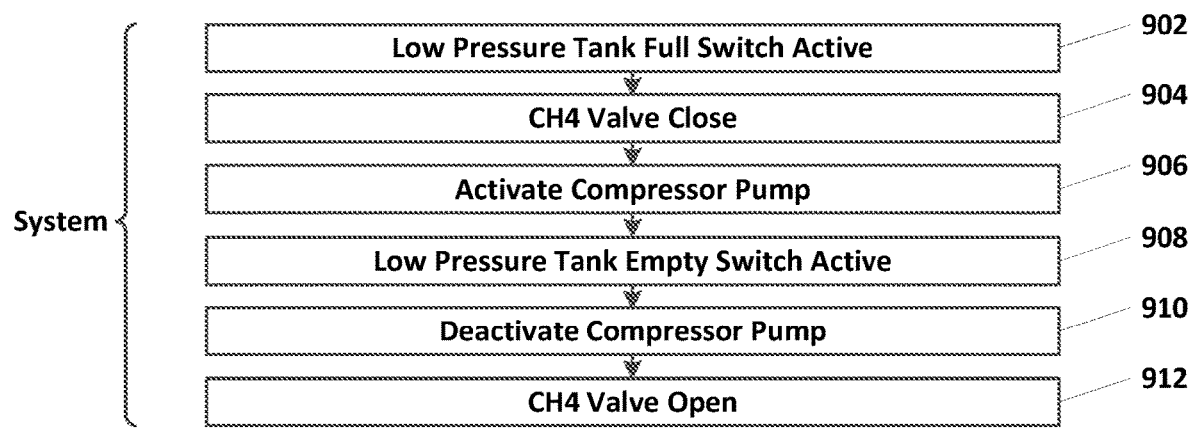
FIG. 9 illustrates embodiments of steps in a method.
Figure 10:
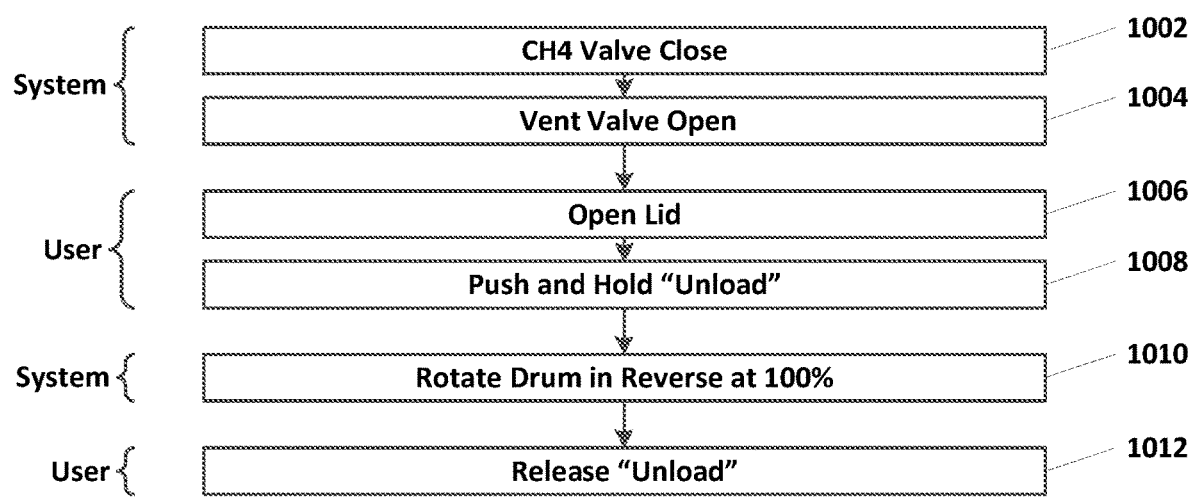
FIG. 10 illustrates embodiments of steps in a method.

The run mode and compressor modes illustrated in FIGS. 8 and 9 repeat until the bio-degradable material has been substantially converted to methane gas and other products, at which time, the cycle complete mode begins. At 1002, computer 302 causes the methane valve to close, and at 1004 the vent valve is opened.

At 1006 the user opens the chamber by removing cover 104, and at 1008 a activates the unload process by pressing and holding an associated button. At 1010, computer 302 causes the chamber to rotate in reverse at 100% until the user releases the associated button at 1012.

The system independently monitors and stores a number of factors, some of which are used during the process to adjust system parameters, and others are stored to maintain records of the process. Those factors include ambient temperature, pressure in the high-pressure tank, battery charge/voltage, chamber rotations, compressor activity, carbon dioxide level or pressure in the supply tank, and dates and times corresponding to those factors and measured events.

It can be helpful to initially process some types of bio-degradable material so that the physical size is reduced. For example, grass clippings and general garden clippings may not need to be chopped or shredded. However, thicker and more fibrous materials, such as branches, may benefit from some initial processing or shredding.

Although not illustrated, in one embodiment the system may also include an oxygen sensor in chamber 102. This can help to determine if there is a leak that is allowing oxygen to enter the chamber. The oxygen sensor can also help monitor the initial system start-up. When the system first starts after the cover is placed on chamber 102, the oxygen sensor will generally show that the oxygen level is close to ambient conditions. As the process starts, the oxygen is consumed by aerobic reactions, and eventually the oxygen content gets low enough that the anaerobic reaction begins to dominate, where methane gas production begins.

Although illustrative embodiments have been described herein in detail, it should be noted and will be appreciated by those skilled in the art that numerous variations may be made within the scope of this invention without departing from the principle of this invention and without sacrificing its chief advantages. For example features that appear in one embodiment of a particular figure are also applicable to embodiments that are illustrated in other figures.

Unless otherwise specifically stated, the terms and expressions have been used herein as terms of description and not terms of limitation. There is no intention to use the terms or expressions to exclude any equivalents of features shown and described or portions thereof and this invention should be defined in accordance with the claims that follow.

The invention claimed is:

1. A processing apparatus for anaerobic treatment of bio-degradable material to produce a combustible gas, comprising:
    a sealable chamber configured to hold the bio-degradable material, the chamber including at least:
        a plurality of internal mixing blades;
        a removable cover with a sealing ring to seal the cover to the chamber;
        a rotating seal in the cover, the rotating seal having a first hollow cylindrical component affixed to the cover, and a second hollow cylindrical component cooperating with and rotatable with respect to the first hollow cylindrical component; and
        a manifold affixed to the second hollow cylindrical component, the manifold including at least a first gas connection for removing a first combustible gas from the chamber and a second gas connection for adding a second gas to the chamber, the second gas to displace oxygen in the chamber;
    a drive unit, configured to at least intermittently rotate the chamber;
    a filter configured to filter the first combustible gas; and
    a first gas storage tank configured to store the first combustible gas.

2. The apparatus according to claim 1, further comprising:
    a second gas storage tank; and
    a compressor connected to both the first gas storage tank and the second gas storage tank, the compressor configured to compress and transfer the first combustible gas from the first gas storage tank to the second gas storage tank.

3. The apparatus according to claim 2, further comprising a sensor configured to activate the compressor based at least on a volume of gas in the first gas storage tank.

4. The apparatus according to claim 1, further comprising:
    a generator configured to burn the first combustible gas.

5. The apparatus according to claim 1, further comprising:
    a generator configured to provide power to the drive unit.

6. The apparatus according to claim 1, wherein the sealable chamber is cylindrical.

7. The apparatus according to claim 1, wherein the internal mixing blades are attached to an inner surface of the chamber, and the internal mixing blades are configured to mix material in the chamber when the chamber is rotated.

8. The apparatus according to claim 1, wherein the filter is an activated carbon filter or a water bubble filter.

9. The apparatus according to claim 1, further comprising a control unit configured to cause activation of the drive unit.

10. The apparatus according to claim 1, further comprising a control unit configured to cause activation of a compressor.

11. The apparatus according to claim 1, further comprising a control unit configured to cause activation of a generator.

12. The apparatus according to claim 1, further comprising a control unit, the control unit receiving data representing at least one of: a temperature value inside the chamber, a temperature value outside the chamber, a gas flow rate, a moisture level of material inside the chamber, or a value representing volume of gas in the first gas storage tank.

13. The apparatus according to claim 1, further comprising at least one battery configured to provide power to the drive unit.

14. The apparatus according to claim 1, further comprising a support mount for the chamber configured to hold a rotational axis of the chamber at an inclined angle relative to a local earth surface.

* * * * *